United States Patent [19]

Katayama et al.

[11] Patent Number: 5,698,540
[45] Date of Patent: Dec. 16, 1997

[54] STABILIZED PESTICIDAL COMPOSITION CONTAINING ACEPHATE

[75] Inventors: Yasuyuki Katayama, Osaka-fu; Toshiro Ohtsubo, Hyogo-ken, both of Japan

[73] Assignee: Sumitomo Chemical Company, Limited, Osaka, Japan

[21] Appl. No.: 386,626

[22] Filed: Feb. 10, 1995

[30] Foreign Application Priority Data

Feb. 10, 1994 [JP] Japan ................................ 6-016761

[51] Int. Cl.$^6$ ........................ A01N 57/28; C07F 9/24
[52] U.S. Cl. ........................ 514/120; 558/71; 558/178
[58] Field of Search ........................ 514/120; 558/71, 558/178

[56] References Cited

U.S. PATENT DOCUMENTS

| | | | |
|---|---|---|---|
| 3,716,600 | 2/1973 | Magee | 260/959 |
| 3,845,172 | 10/1974 | Magee | 260/956 |
| 4,595,679 | 6/1986 | Broadbent | 514/120 X |
| 5,071,463 | 12/1991 | Narayanan et al. | 71/79 |
| 5,160,528 | 11/1992 | Chaudhuri et al. | 71/79 |
| 5,298,501 | 3/1994 | Cummings | 514/120 |
| 5,352,674 | 10/1994 | Cummings | 514/120 |
| 5,488,043 | 1/1996 | Yamada et al. | 514/120 |

OTHER PUBLICATIONS

*The Pesticide Manual*, 8th Edition, p. 1 (1987, The British Crop Protection Council).

*Primary Examiner*—Michael G. Ambrose
*Attorney, Agent, or Firm*—Sughrue, Mion, Zinn, Macpeak & Seas, PLLC

[57] ABSTRACT

A liquid pesticidal composition including Acephate and one or more N-alkyl-2-pyrrolidones, and methods for stabilizing and inhibiting decomposition of Acephate by adding one or more N-alkyl-2-pyrrolidones to Acephate. The storage stability of Acephate bulk or Acephate in an Acephate-containing liquid pesticidal composition is improved by addition of the N-alkyl-2-pyrrolidone(s).

21 Claims, No Drawings

STABILIZED PESTICIDAL COMPOSITION CONTAINING ACEPHATE

BACKGROUND OF THE INVENTION

1. Field of the Invention

The present invention is directed to a stabilized liquid pesticidal composition including O,S-dimethyl acetylphosphoramidothioate, commonly known as Acephate, and the stabilization of Acephate.

2. Description of the Related Art

Acephate is an insecticidal active compound described in, for example, *The Pesticide Manual*, 8th Edition, page 1 (1987, The British Crop Protection Council). Acephate has the following structural formula:

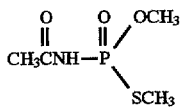

See U.S. Pat. Nos. 3,716,600 and 3,645,172, the disclosures of which are both incorporated herein by reference, regarding the preparation and activity of Acephate. Acephate is currently used as an active ingredient of agricultural insecticides due to its efficacy in killing and controlling various kinds of pests and insects.

However, Acephate is not very stable in conventional pesticidal formulations, such that a vigorous decomposition of Acephate in conventional formulations takes place depending on storing conditions and, as a result, the insecticidal activity of Acephate sometimes cannot be fully utilized.

Accordingly, there is a need for a stable pesticidal composition comprising Acephate.

SUMMARY OF THE INVENTION

After an extensive study of the above problems, the present inventors have discovered that N-alkyl-2-pyrrolidones inhibit decomposition of Acephate and stabilize Acephate.

Thus, the present invention is directed to a liquid pesticidal composition comprising Acephate and one or more N-alkyl-2-pyrrolidones, stabilized Acephate and a method of stabilization of Acephate which comprises adding one or more N-alkyl-2-pyrrolidones to Acephate.

DETAILED DESCRIPTION OF THE PREFERRED EMBODIMENTS

Acephate in the liquid pesticidal composition according to the present invention can effectively exhibit its insecticidal activity since decomposition of the Acephate are inhibited or prevented such that the Acephate are stabilized. This is achieved by addition of one or more N-alkyl-2-pyrrolidones.

Suitable N-alkyl-2-pyrrolidones for use in the present invention include 2-pyrrolidones whose hydrogen atom on the nitrogen atom is substituted by an alkyl group. Suitable compounds include, for example, N—($C_1$–$C_5$)alkyl-2-pyrrolidones, i.e., N-methyl-2-pyrrolidone, N-ethyl-2-pyrrolidone, N-propyl-2-pyrrolidone, N-butyl-2-pyrrolidone, and N-pentyl-2-pyrrolidone, preferably N-methyl-2-pyrrolidone. Other suitable N-alkyl-2-pyrrolidones will be apparent to one skilled in the art.

The amount of N-alkyl-2-pyrrolidone effective for stabilizing Acephate is preferably about 0.1–100 parts, more preferably about 0.5–10 parts by weight, based on 1 part by weight of Acephate.

The amount of Acephate in the liquid pesticidal composition of the present invention is preferably about 0.5–70%, more preferably about 5–50% by weight, based on the weight of the liquid pesticidal composition, and that of N-alkyl-2-pyrrolidone, as a stabilizer in the liquid pesticidal composition, is an amount capable of stabilizing Acephate and preferably is about 1–99%, more preferably about 50–90% by weight, based on the weight of the liquid pesticidal composition.

The liquid pesticidal composition of the present invention includes Acephate and one or more N-alkyl-2-pyrrolidones, but may further include an emulsifier, solvent and/or other pesticidal active ingredients.

Any suitable emulsifier may be used in the present invention. Examples of suitable emulsifiers include anionic surface active agents, such as sulfonates, including alkyl sulfonates, alkyl aryl sulfonate and the like, and nonionic surface active agents, such as polyoxyethylene alkyl ether, polyoxyethylene alkyl aryl ether, polyoxyethyene aryl aryl ether, and the like. Other suitable emulsifiers will be apparent to one skilled in the art. The amount of the emulsifier utilized in the present invention is preferably about 0.5–30%, more preferably about 2–10% by weight, based on the total weight of the liquid pesticidal composition of the present invention.

Any suitable solvent may be used in the present invention. Examples of suitable solvents include aromatic hydrocarbons, such as alkylbenzenes including toluene, xylene, ethylbenzene, naphthalene, alkylnaphthalenes, triarylalkanes and the like; saturated aliphatic hydrocarbons; unsaturated aliphatic hydrocarbons; alcohols, such as monohydric alcohols including methyl alcohol, ethyl alcohol, isopropyl alcohol and the like, polyalkylene glycols including diethylene glycol, triethylene glycol, dipropylene glycol and the like; ketones, such as cyclohexanone, methyl butyl ketone and the like; esters, such as alkyl acetate and the like; ethers, such as alkyl ether, alkyl aryl ether and the like; nitriles, such as acetonitrile and the like. Other suitable solvents will be apparent to one skilled in the art. The amount of the solvent utilized in the present invention is preferably about 10–90%, more preferably about 20–70% by weight, based on the weight of the total liquid pesticidal composition of the present invention.

Any suitable other pesticidal active ingredient may be used in the liquid pesticidal composition of the present invention. Examples of other pesticidal active ingredients include pyrethroid compounds, such as Fenpropathrin (2,2,3,3-tetramethylcyclopropane carboxylic acid cyano(3-phenoxyphenyl)methyl ester), Fenvalerate (4-chloro-α-(1-methylethyl) benzeneacetic acid cyano(3-phenoxyphenyl methyl ester) and Esfenvalerate ((S,S)-isomer of Fenvalerate). Other suitable pesticidal active ingredients will be apparent to one skilled in the art. The amount of the other pesticidal active ingredient utilized in the present invention is preferably about 0.1–50%, more preferably about 1–20% by weight, based on the total weight of the liquid pesticidal composition.

Any suitable method may be used to prepare the liquid pesticidal composition of the present invention. For example, the liquid pesticidal composition of the present invention may be prepared by combining Acephate and one or more N-alkyl-2-pyrrolidones, and if desired, one or more emulsifiers, one or more solvents, one or more other pesticidal active ingredients and the like, and mixing the same together. Other suitable methods will be apparent to one skilled in the art.

The present invention will now be explained in detail by reference to the following formulation examples and a test example, which should not be construed as limiting the present invention.

Formulation Example 1

A liquid pesticidal composition in accordance with the invention was obtained by mixing 15 parts by weight Acephate, 10 parts by weight polyoxyethylene styryl phenyl ether and 75 parts by weight N-methyl-2-pyrrolidone with stirring.

Formulation Example 2

A liquid pesticidal composition in accordance with the invention was obtained by mixing 30 parts by weight Acephate, 10 parts by weight polyoxyethylene styryl phenyl ether and 60 parts by weight N-methyl-2-pyrrolidone with stirring.

Test Example

Liquid pesticidal compositions obtained in accordance with the above Formulation Examples 1 and 2 were sealed into respective 25 ml glass ampules and stored in a thermostatic box at 40° C. and 50° C. for a month (30 days). The amount of Acephate remaining in the formulations after storage was measured by gas chromatography and the rate of decomposition of the Acephate was calculated according to the following equation:

$$\text{Rate of decomposition (\%)} = 100 - 100 \times \frac{\text{amount of Acephate after storage}}{\text{amount of Acephate before storage}}$$

Further, the rates of decomposition of Acephate in Comparative Formulations 1 and 2 which were prepared in the same manner as Formulations 1 and 2, respectively, except that methyl alcohol was used in place of N-methyl-2-pyrrolidone, were also calculated.

The results are shown in the below Table.

TABLE 1

| Formulation | Rate of Decomposition After Storage at 40° C. for 1 month (%) | Rate of Decomposition After Storage at 50° C. for 1 month (%) |
|---|---|---|
| Example 1 | 0.2 | 6.0 |
| Example 2 | 1.3 | 5.7 |
| Comparative Formulation 1 | 17.5 | 38.6 |
| Comparative Formulation 2 | 18.1 | 34.5 |

The foregoing examples and comparative examples confirm that the storage stability of Acephate bulk or Acephate in an Acephate-containing liquid pesticidal composition is improved by addition of N-alkyl-2-pyrrolidone(s).

Although the present invention has been described in connection with preferred embodiments thereof, many other variations and modifications will become apparent to one skilled in the art without departing from the scope of the invention. It is preferred, therefore, that the present invention not be limited by the specific disclosure herein, but only by the appended claims.

What is claimed is:

1. A liquid pesticidal composition, comprising a pesticidally effective amount of O,S-dimethyl acetylphosphoramidothioate and an N-alkyl-2-pyrrolidone in an amount effective for stabilizing the O,S-dimethyl acetylphosphoramidothioate.

2. The liquid pesticidal composition according to claim 1, wherein the N-alkyl-2-pyrrolidone is an N—($C_1$–$C_5$)alkyl-2-pyrrolidone.

3. The liquid pesticidal composition according to claim 2, wherein the N—($C_1$–$C_5$)alkyl-2-pyrrolidone is N-methyl-2-pyrrolidone.

4. The liquid pesticidal composition according to claim 1, wherein the N-alkyl-2-pyrrolidone is present in an amount of 0.1–100 parts by weight, based on 1 part by weight of the O,S-dimethyl acetylphosphoramidothioate.

5. The liquid pesticidal composition according to claim 4, wherein the N-alkyl-2-pyrrolidone is present in an amount of 0.5–10 parts by weight, based on 1 part by weight of the O,S-dimethyl acetylphosphoramidothioate.

6. The liquid pesticidal composition according to claim 1, wherein the O,S-dimethyl acetylphosphoramidothioate is present in an amount of 0.5–70% by weight based upon the weight of the composition.

7. The liquid pesticidal composition according to claim 6, wherein the O,S-dimethyl acetylphosphoramidothioate is present in an amount of 5–50% by weight based upon the weight of the composition.

8. The composition according to claim 1, wherein the amount of N-alkyl-2-pyrrolidone is 50–90% by weight based on the weight of the liquid pesticidal composition.

9. The composition according to claim 1, wherein the composition has a one-month decomposition rate at about 40° C. of below 17.5%.

10. A method for stabilizing O,S-dimethyl acetylphosphoramidothioate, comprising the step of adding to the O,S-dimethyl acetylphosphoramidothioate an amount of an N-2-alkyl-pyrrolidone effective for stabilizing the O,S-dimethyl acetylphosphoramidothioate.

11. The method according to claim 10, wherein the N-alkyl-2-pyrrolidone is an N—($C_1$–$C_5$) alkyl-2-pyrrolidone.

12. The method according to claim 11, wherein the N—($C_1$–$C_5$)alkyl-2-pyrrolidone is N-methyl-2-pyrrolidone.

13. The method according to claim 10, wherein the amount of N-alkyl-2-pyrrolidone is 0.1–100 parts by weight based on 1 part by weight of the O,S-dimethyl acetylphosphoramidothioate.

14. The method according to claim 13, wherein the amount of N-alkyl-2-pyrrolidone is 0.5–10 parts by weight based on 1 part by weight of the O,S-dimethyl acetylphosphoramidothioate.

15. The method according to claim 10, wherein the O,S-dimethyl acetylphosphoramidothioate is present in a liquid pesticidal composition.

16. A method for inhibiting decomposition of O,S-dimethyl acetylphosphoramidothioate, comprising the step of adding to the O,S-dimethyl-acetylphosphoramidothioate an amount of N-alkyl-2-pyrrolidone effective for inhibiting decomposition of the O,S-dimethyl acetylphosphoramidothioate.

17. The method according to claim 16, wherein the N-alkyl-2-pyrrolidone is an N—($C_1$–$C_5$)alkyl-2-pyrrolidone.

18. The method according to claim 17, wherein the N—($C_1$–$C_5$) alkyl-2-pyrrolidone is N-methyl-2-pyrrolidone.

19. The method according to claim 16, wherein the amount of N-alkyl-2-pyrrolidone is 0.1–100 parts by weight based on 1 part by weight of the O,S-dimethyl acetylphosphoramidothioate.

20. The method according to claim 19, wherein the amount of N-alkyl-2-pyrrolidone is 0.5–10 parts by weight based on 1 part by weight of the O,S-dimethyl acetylphosphoramidothioate.

21. The method according to claim 16, wherein the O,S-dimethyl acetylphosphoramidothioate is present in a liquid pesticidal composition.

* * * * *